United States Patent
Park et al.

(10) Patent No.: US 11,441,745 B2
(45) Date of Patent: Sep. 13, 2022

(54) LIGHT EMITTING DEVICE AND CONTROL METHOD THEREOF

(71) Applicant: Samsung Electronics Co., Ltd., Suwon-si (KR)

(72) Inventors: Sooyeon Park, Seoul (KR); Myungkyum Kim, Incheon (KR); Minjun Kim, Seoul (KR); Taesik Cho, Siheung-si (KR); Jeongho Han, Bucheon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 196 days.

(21) Appl. No.: 17/069,319

(22) Filed: Oct. 13, 2020

(65) Prior Publication Data

US 2021/0108771 A1  Apr. 15, 2021

(30) Foreign Application Priority Data

Oct. 15, 2019 (KR) .......................... 10-2019-0127478

(51) Int. Cl.
*H05B 45/20* (2020.01)
*H05B 47/11* (2020.01)
*F21V 14/02* (2006.01)
*F21S 8/02* (2006.01)
*F21V 23/00* (2015.01)
(Continued)

(52) U.S. Cl.
CPC .............. *F21S 8/024* (2013.01); *F21V 14/02* (2013.01); *F21V 23/009* (2013.01); *H05B 45/18* (2020.01); *H05B 45/20* (2020.01); *H05B 45/3577* (2020.01); *H05B 47/11* (2020.01)

(58) Field of Classification Search
None
See application file for complete search history.

(56) References Cited

U.S. PATENT DOCUMENTS

2009/0251057 A1  10/2009  Son et al.
2013/0293152 A1*  11/2013  Barroso ................. H05B 45/20
                                                        315/307
2014/0070724 A1   3/2014  Gould et al.
(Continued)

FOREIGN PATENT DOCUMENTS

KR  10-2011-0046107 A   5/2011
KR  10-1155024 B1        6/2012
(Continued)

OTHER PUBLICATIONS

International Search Report dated Jan. 19, 2021, issued in International Application No. PCT/KR2020/013839.

*Primary Examiner* — Dedei K Hammond
(74) *Attorney, Agent, or Firm* — Jefferson IP Law, LLP

(57) ABSTRACT

A light emitting device is provided. The light emitting device includes a first light emitter comprising a plurality of light emitting elements configured to emit light in a visible light region, a second light emitter comprising a plurality of light emitting elements configured to emit light in an ultraviolet B (UVB) region, and at least one processor configured to control the first light emitter and the second light emitter so that a sum of an intensity of light emitted from the first light emitter and an intensity of light emitted from the second light emitter is greater than or equal to a threshold illuminance value.

18 Claims, 11 Drawing Sheets

(51) Int. Cl.
      *H05B 45/3577*    (2020.01)
      *H05B 45/18*      (2020.01)

(56) References Cited

U.S. PATENT DOCUMENTS

2019/0166672 A1    5/2019   Lee
2019/0242539 A1*  8/2019   Roberts .................. F21S 8/006

FOREIGN PATENT DOCUMENTS

| | | | |
|---|---|---|---|
| KR | 10-1318968 B1 | 10/2013 | |
| KR | 10-2015-0121446 A | 10/2015 | |
| KR | 10-1562208 B1 | 10/2015 | |
| KR | 10-2016-0057501 A | 5/2016 | |
| KR | 10-1680488 B1 | 11/2016 | |
| KR | 101680488 B1 * | 11/2016 | ............... A61N 5/06 |
| KR | 10-2017-0080118 A | 7/2017 | |
| KR | 10-2017-0120772 A | 11/2017 | |
| KR | 10-2017-0136000 A | 12/2017 | |
| KR | 10-2018-0114219 A | 10/2018 | |
| KR | 10-1910488 B1 | 10/2018 | |
| KR | 10-2019-0105844 A | 9/2019 | |
| KR | 10-2029453 B1 | 10/2019 | |
| WO | 2014/075721 A1 | 5/2014 | |
| WO | 2017/152940 A1 | 9/2017 | |

* cited by examiner

LIGHT EMITTING DEVICE AND CONTROL METHOD THEREOF

CROSS-REFERENCE TO RELATED APPLICATION(S)

This application is based on and claims priority under 35 U.S.C. § 119(a) of a Korean patent application number 10-2019-0127478, filed on Oct. 15, 2019, in the Korean Intellectual Property Office, the disclosure of which is incorporated by reference herein in its entirety.

BACKGROUND

1. Field

The disclosure relates to a light emitting device and a control method thereof. More particularly, the disclosure relates to a light emitting device which includes a plurality of light emitting elements and a control method thereof.

2. Description of Related Art

Natural light induces synthesis of a neurotransmitter and vitamin D necessary for a healthy life of a human and thus, a human needs to be exposed to natural light for a certain period of time or longer.

In recent years, amid a rapidly changing life pattern, modern people are primarily living in indoor and a closed space, and the time spent for outdoor activity is gradually decreasing. As the time to be exposed to natural light is reduced, lack of vitamin D and serotonin may occur, and there is a worry of exposure to diseases such as osteoporosis and depression.

There is a need for a light emitting device that provides light similar to natural light to modern people who mainly live indoor and thus are not directly exposed to natural light, to induce synthesis of neurotransmitters such as vitamin D and serotonin.

In addition, there is a need for a light emitting device that induces the synthesis of a neurotransmitter such as vitamin D, serotonin, or the like, without damage to skin by exposing to an appropriate amount of ultraviolet light, rather than directly exposing to strong sunlight.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a light emitting device emitting light similar to natural light and a control method thereof.

Additional aspects will be set forth in part in the description which follows and, in part, will be apparent from the description, or may be learned by practice of the presented embodiments.

In accordance with an aspect of the disclosure, a light emitting device is provided. The light emitting device includes a first light emitter comprising a plurality of light emitting elements configured to emit light in a visible light region, a second light emitter comprising a plurality of light emitting elements configured to emit light in an ultraviolet B (UVB) region, and at least one processor configured to control the first light emitter and the second light emitter so that a sum of an intensity of light emitted from the first light emitter and an intensity of light emitted from the second light emitter is greater than or equal to a threshold illuminance value.

In accordance with another aspect of the disclosure, a control method of a light emitting device is provided. The control method includes causing a first light emitter comprising a plurality of light emitting elements configured to emit light in a visible light region to emit light, causing a second light emitter comprising a plurality of light emitting elements configured to emit light in an ultraviolet B region to emit light, and controlling the first light emitter and the second light emitter so that a sum of intensity of light emitted from the first light emitter and intensity of light emitted from the second light emitter is greater than or equal to a threshold illuminance value.

According to various embodiments, by emitting light similar to natural light even in a closed indoor space, there is an effect of reducing risk for a user to be exposed to various diseases by inducing in-vivo vitamin D synthesis and generating serotonin which is a neurotransmitter.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
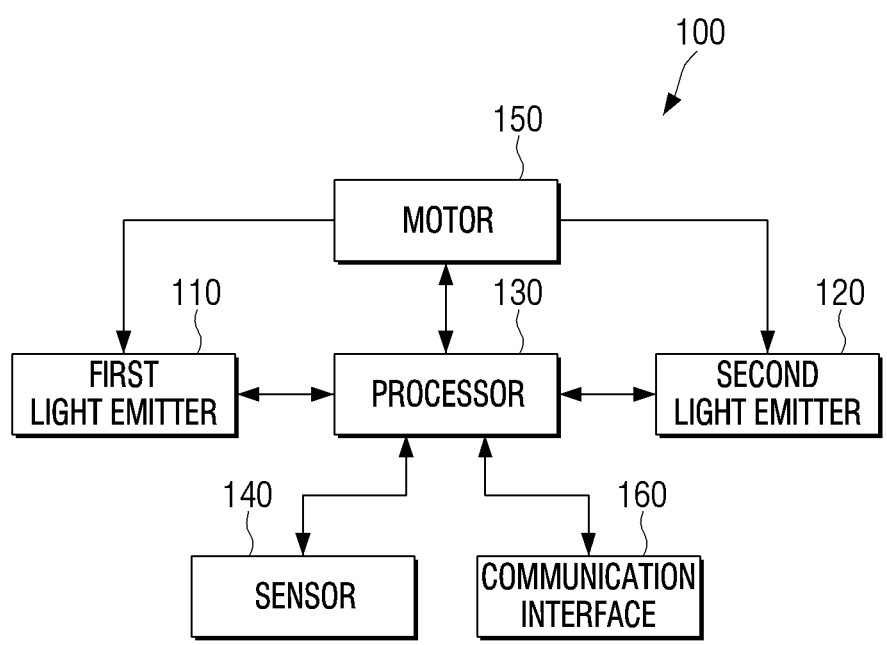
FIG. 1 is a block diagram illustrating a configuration of a light emitting device according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Since the disclosure may be variously modified and have several embodiments, specific non-limiting example embodiments of the disclosure will be illustrated in the drawings and be described in detail in the detailed description. However, it is to be understood that the disclosure is not limited to specific non-limiting example embodiments, but includes all modifications, equivalents, and substitutions without departing from the scope and spirit of the disclosure. When it is decided that a detailed description for the known art related to the disclosure may obscure the gist of the disclosure, the detailed description will be omitted.

As used herein, the terms "first," "second," or the like may identify corresponding components, regardless of importance of order, and are used to distinguish a component from another without limiting the components.

Singular forms are intended to include plural forms unless the context clearly indicates otherwise. It will be further understood that terms "include" or "formed of" used in the present specification specify the presence of features, numerals, steps, operations, components, parts, or combinations thereof mentioned in the present specification, but do not preclude the presence or addition of one or more other features, numerals, steps, operations, components, parts, or combinations thereof.

A term such as "module," "unit," "part," and so on is used to refer to an element that performs at least one function or operation, and such element may be implemented as hardware or software, or a combination of hardware and software. Further, other than when each of a plurality of "modules," "units," "parts," and the like must be realized in an individual hardware, the components may be integrated in at least one module and be realized in at least one processor (not shown).

Hereinafter, non-limiting example embodiments of the disclosure will be described in detail with reference to the accompanying drawings so that those skilled in the art to which the disclosure pertains may easily practice the disclosure. However, the disclosure may be implemented in various different forms and is not limited to embodiments described herein. In addition, in the drawings, portions unrelated to the description will be omitted, and similar portions will be denoted by similar reference numerals throughout the specification.

FIG. 1 is a block diagram illustrating a configuration of a light emitting device according to an embodiment of the disclosure.

Referring to FIG. 1, a light emitting device 100 according to an embodiment includes a first light emitter 110, a second light emitter 120, and a processor 130.

The light emitting device 100 according to various embodiments may include at least one of, for example, a smartphone, a tablet personal computer (PC), a mobile phone, a video phone, an e-book reader, a desktop PC, a laptop PC, a netbook computer, a workstation, a server, a personal digital assistant (PDA), a portable multimedia player (PMP), an MP3 player, a medical device, a camera, or a wearable device. A wearable device may include at least one of an accessory type (e.g., a watch, a ring, a bracelet, an ankle bracelet, a necklace, a pair of glasses, a contact lens or a head-mounted-device (HMD)); a fabric or a garment-embedded type (e.g.: electronic cloth); skin-attached type (e.g., a skin pad or a tattoo); or a bio-implantable circuit. In some embodiments, the electronic device may include at least one of, for example, a television, a digital video disk (DVD) player, an audio system, a refrigerator, air-conditioner, a cleaner, an oven, a microwave, a washing machine, an air purifier, a set top box, a home automation control panel, a security control panel, a media box (e.g., SAMSUNG HOMESYNC™, APPLE TV™, or GOOGLE TV™), a game console (e.g., XBOX™, PLAYSTATION™), an electronic dictionary, an electronic key, a camcorder, or an electronic frame.

In other embodiments, the electronic device may include at least one of a variety of medical devices (e.g., various portable medical measurement devices such as a blood glucose meter, a heart rate meter, a blood pressure meter, or a temperature measuring device), magnetic resonance angiography (MRA), magnetic resonance imaging (MRI), computed tomography (CT), or ultrasonic wave device, etc.), a navigation system, a global navigation satellite system (GNSS), an event data recorder (EDR), a flight data recorder (FDR), an automotive infotainment devices, a marine electronic equipment (e.g., marine navigation devices, gyro compasses, etc.), avionics, a security device, a car head unit, industrial or domestic robots, a drone, an automated teller machine (ATM), a point of sale (POS) of a store, or an Internet of Things (IoT) device (e.g., light bulbs, sensors, sprinkler devices, fire alarms, thermostats, street lights, toasters, exercise equipment, hot water tanks, heater, boiler, etc.).

For convenience, the light emitting device 100 is described as a lighting device. The lighting device may include, but is not limited to, a basic lighting, a mood lighting, a stand lighting, a decorative lighting, or the like, in a living room, a room, a balcony, a kitchen, a bathroom, stairs, a front door, or the like.

According to an embodiment, the first light emitter 110 may include a plurality of light emitting elements emitted by a rectified voltage. Here, the plurality of light emitting elements included in the first light emitter 110 may emit light in a visible light region. Visible light refers to light that is detectable in the human eye with light having a wavelength of about 380-750 nm.

Each of the plurality of light emitting elements included in the first light emitter 110 according to an embodiment may be implemented as at least one of a white light emitting element, a red light emitting element, a green light emitting element, or a blue light emitting element. The first light emitter 110 according to an embodiment may include a multi-color light emitting element such as white, red, green, or blue such that the light emitted from the first light emitter 110 may have a spectral distribution that varies continuously in the wavelength range (e.g., 400 nm to 700 nm) of the visible light.

The second light emitter 120 according to an embodiment may include a plurality of light emitting elements that emit light in an ultraviolet region. For example, the second light emitter 120 may include a plurality of light emitting elements that emit light having a wavelength of the ultraviolet B (UVB) region. Here, the wavelength of the UVB region may be in the range of 280 nm to 320 nm.

The light in the ultraviolet region may be divided into UVA, UVB, and UVC depending on the wavelength. For example, the light corresponding to the UVA has a wavelength of 320 nm to 400 nm, and has a weak energy and a long wavelength. Light corresponding to UVB has a wavelength of 280 nm to 320 nm and has the effect of anion generation, vitamin D generation, sun tanning of skin, or the like. The light corresponding to the UVC has a wavelength of 100 nm to 280 nm and has strong energy. Accordingly, the light corresponding to the UVC has the effect of generating ozone, sterilizing, deodorizing, or the like.

The second light emitter 120 according to an embodiment may emit light having a wavelength of a UVB region using a plurality of light emitting elements to induce synthesis of vitamin D in the body of the user. For example, when 7-Dehydrochorsterin of human skin receives light in the UVB region of wavelengths from 280 nm to 320 nm included in natural light of the Sun, vitamin D is synthesized in the human body. According to an embodiment, the light emitting device 100 may emit light in a UVB region, thereby inducing in-vivo synthesis of vitamin D even in a closed space, an underground space, an indoor space, etc., at which natural light does not arrive.

The light emitting device 100 according to various embodiments may prevent side effects of lack of vitamin D such as rickets, osteomalacia, dizziness, or the like, by inducting in-vivo synthesis of vitamin D even in a situation where the user is not exposed to natural light.

The processor 130 controls overall operation of the light emitting device 100.

The processor 130 may include various processing circuitry and may, for example, and without limitation, be implemented with a digital signal processor (DSP), a microprocessor, and a time controller (TCON) which process a digital image signal, but this is not limited thereto. The processor 130 may include, for example, and without limitation, one or more among a central processing unit (CPU), a micro controller unit (MCU), a micro processing unit (MPU), a controller, an application processor (AP), a graphics-processing unit (GPU), a communication processor (CP), an advanced reduced instruction set computing (RISC) machine (ARM) processor, or the like, or may be defined as a corresponding term. The processor 130 may be implemented in a system on chip (SoC) type or a large scale integration (LSI) type which a processing algorithm is built therein or in a field programmable gate array (FPGA) type.

The processor 130 according to an embodiment may control the first light emitter 110 and the second light emitter 120 so that the sum of the intensity of light emitting from each of the first light emitter 110 and the second light emitter 120 get to be greater than or equal to a threshold illuminance value. For example, the processor 130 may control the first light emitter 110 and the second light emitter 120 so that the sum of the intensity of light emitted from each of the first light emitter 110 and the second light emitter 120 is to be greater than or equal to 3000 lx.

The natural light of the Sun may induce in-vivo synthesis of vitamin D, and may also induce generation or activation of various hormones, neurotransmitter, or the like, in the body.

In order to generate serotonin (5-Hydroxytryptamine (5-HT)), which is one of neurotransmitters, natural light is required, in addition to dietary intake and sleep. For example, when light having an intensity of at least about 3000 lx reaches a retina of a human, the light stimulates nerve cells to induce the production of serotonin.

The neurotransmitter such as serotonin is closely related to happiness among various feelings which a human may feel and lack of serotonin may cause depression, character disorder, eating disorder, or anxiety disorder, and thus, there is need for a human to be exposed to natural light to prevent lack of serotonin.

The light emitting device 100 according to various embodiments may emit light having an intensity above a threshold illuminance value for inducing the production of serotonin by stimulating nerve cells. As the processor 130 controls the first and second light emitters 110 and 120 to emit light having an intensity greater than or equal to a threshold illuminance value, the light emitting device 100 may induce the serotonin to be synthesized in the body of the user located in an indoor space in which the light emitting device 100 is positioned in a situation where there is no natural light of the Sun.

The threshold illuminance value may have a variety of values, in addition to 3000 lx. According to one embodiment, the sum of the intensities of light emitted from each of the first and second light emitters 110 and 120 may be in the range of 1,500 to 10,000 lx. The specific illuminance value is merely exemplary and is not limited thereto, and may be set to have an illuminance value other than the range of 1,500 to 10,000 lx. For example, various changes may be made in accordance with the settings of the user, the manufacturing purpose of a manufacturer, or the like.

The embodiment format of the first light emitter 110 and the second light emitter 120 included in the light emitting device 100 will be described below.

Figure 2:
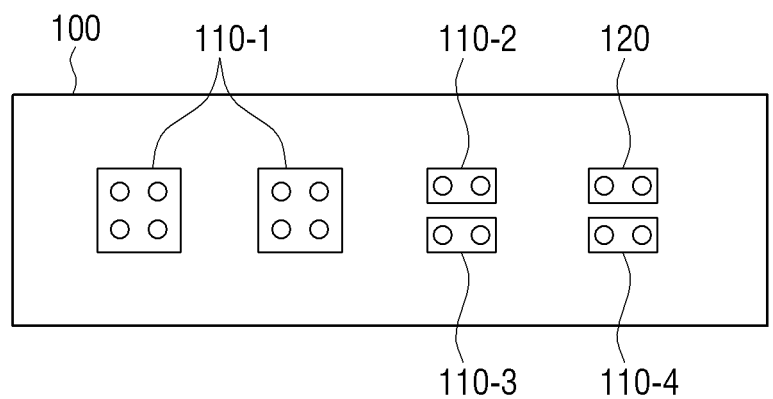
FIG. 2 is a diagram illustrating a first light emitter and a second light emitter according to an embodiment of the disclosure.

FIG. 2 is a diagram illustrating the first light emitter and the second light emitter according to an embodiment of the disclosure.

Referring to FIG. 2, the light emitting device 100 includes the first light emitter 110 and the second light emitter 120.

Each of the plurality of light emitting elements included in the first light emitter 110 may be implemented as at least one of a white light emitting element 110-1, a red light emitting element 110-2, a green light emitting element 110-3, or a blue light emitting element 110-4. According to an embodiment, the light emitting element greater than or equal to a threshold ratio among the plurality of light emitting elements included in the first light emitter 110 may be implemented as the white light emitting element 110-1. The remaining light emitting elements among a plurality of light emitting elements may be implemented as at least one of the red light emitting element 110-2, the green light emitting element 110-3, or the blue light emitting element 110-4. The threshold ratio may mean 50% or more. For example, the light source emitted from the first light emitter 110 and the second light emitter 120 may have a size of 24 W, and the light source emitted from the white light emitting element 110-1 among the plurality of light emitting elements included in the first light emitter 110 may have a size of at least 12 W.

The light emitting device 100 according to an embodiment may include a plurality of white light emitting elements 110-1 having high color rendering index (CRI) to have color gamut similar to the natural light of the Sun. The CRI is an index to evaluate to which degree the light source represents an original color of an object, and the light source having high CRI may represent the original color of an object more vividly.

The first light emitter 110 according to an embodiment may implement 50% of the plurality of light emitting elements as white light emitting element 110-1 so that the light emitted from the light emitting device 100 may have high CRI, and implement remaining light emitting elements as at least one of the red light emitting element 110-2, the green light emitting element 110-3 or the blue light emitting element 110-4.

A specific numerical value such as 50% is only one embodiment and is not limited thereto. For example, the first light emitter 110 may be implemented such that, if the intensity of the light emitted from each of the light emitting elements is the same, relatively larger light emitting elements, among the plurality of light emitting elements included in the first light emitter 110, may be implemented as white light emitting elements. As another example, if the intensity of the light emitted from each of the light emitting elements is different, the light emitter 110 may be implemented so that the intensity of light emitted by the white light emitting device is relatively larger than the intensity of light emitted by light emitting elements of remaining colors.

For example, referring to FIG. 2, the first light emitter 110 according to an embodiment may be implemented such as a form including various colors, various power intensity, various numbers of light emitting elements such as two 6 W-sized white light emitting elements 110-1, two 2 W-sized red light emitting elements 110-2, two 2 W-sized green light emitting elements 110-3, two 2 W-sized blue light emitting elements 110-4, or the like. The first light emitter 110 may include a multi-color light emitting element such as white, red, green, or blue based on a predetermined ratio W:R:G:B such that the light emitted from the first light emitter 110 may have a spectral distribution that varies continuously in the wavelength range (e.g., 400 nm to 700 nm) of the visible lights.

The light emitting device 100 may include the second light emitter 120 and the second light emitter 120 may include a plurality of light emitting elements emitting light of the ultraviolet region, for example, UVB region.

The implementation form of the first light emitter 110 and the second light emitter 120 of FIG. 2 is merely exemplary and is not limited thereto. For example, the first light emitter 110 may be implemented as a circular shape, and may include a plurality of light emitting elements. The plurality of light emitting elements included in the second light emitter 120 may be disposed to be adjacent to the first light emitter 110 and as another example, may be disposed between a plurality of light emitting elements included in the first light emitter 110. The rated power of each of each of the plurality of light emitting elements included in the second light emitter 120 may be different.

Hereinafter, the feature of light emitted from the light emitting device 100 will be described.

Figure 3A:
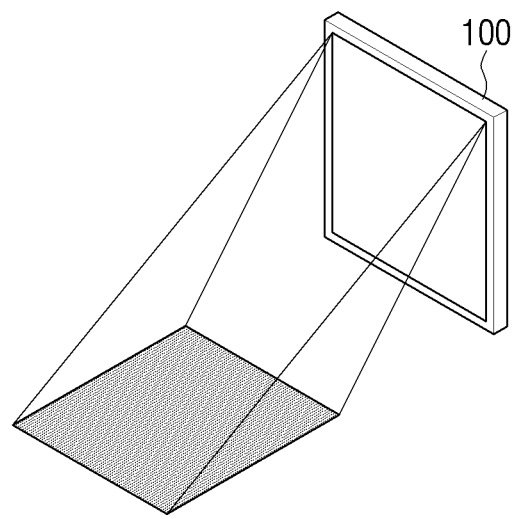
FIG. 3A is a diagram illustrating straightness of light according to an embodiment of the disclosure.

FIG. 3A is a diagram illustrating straightness of light according to an embodiment of the disclosure.

Referring to FIG. 3A, the light emitting device 100 according to an embodiment may include a light collector for collecting and irradiating light. For example, the light emitting device 100 may include a first light collector disposed in a front portion of the first light emitter 110 for collecting and irradiating light emitted from the first light emitter 110. The light emitting device 100 may include the second light emitter disposed at a front portion for collecting and irradiating light from the second light emitter 120.

As illustrated in FIG. 3A, the light emitted from each of the first and second light collects may have a straightness. Here, the light collector may be configured to prevent the diffusion of the light emitted from the light emitter. For example, the light collector may include a light collecting reflector tunnel for collecting the light emitted from the light emitter, and a lens for collecting and irradiating the light. As another example, the light collector has a shape in which a cross-sectional area is widened from an upper side adjacent to the light emitter toward a lower side away from the light emitter, and an opening unit for irradiating light at a lower portion thereof is provided. The inner surface of the light collector may be made of a material to which light may be reflected and collected. For example, the inner surface of the light collector may be formed in a form that a metal material capable of reflecting mirror or light is installed and coated. Since the light emitted from the light emitting device 100 has a straightness, the emitted light may provide a user with an effect similar to the direct incident light through the window.

Figure 3B:
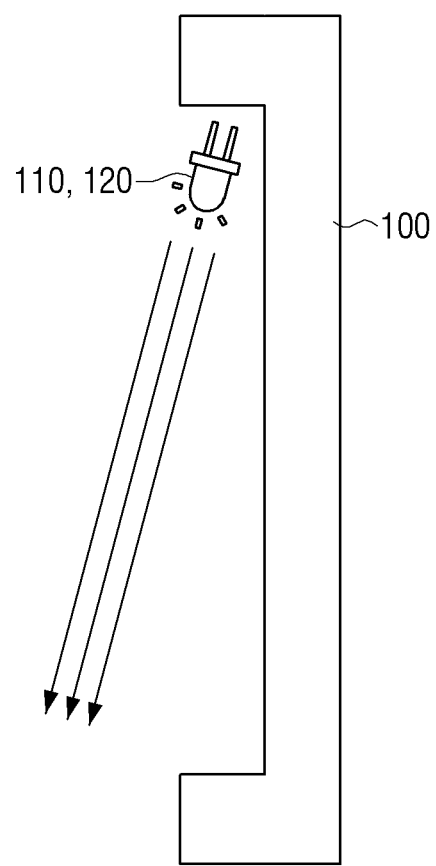
FIG. 3B is a diagram illustrating a side view of a light emitting device according to an embodiment of the disclosure.

FIG. 3B is a diagram illustrating a side view of a light emitting device according to an embodiment of the disclosure.

Referring to FIG. 3B, the light emitting device 100 according to an embodiment may be implemented as a device installable on a wall. The light emitting device 100 may include an outer area (or an edge area). The light emitting device 100 may include a bezel housing the light emitting device 100. The bezel according to an embodiment may be disposed at a form surrounding the outer area of the light emitting device 100.

The first light emitter 110 may be disposed at one side of the light emitting device 100. The one side may refer to a region among an outer region of the light emitting device 100 or an inside region surrounded by the bezel. The second light emitter 120 may be disposed to be adjacent to the first light emitter 110 at one side of the light emitting device 100.

Returning to FIG. 1, the light emitting device 100 according to an embodiment may further include a motor 150. The processor 130 may identify one of the spaces in which the light emitting device 100 is installed based on the current time information, and adjust the light emission direction of the first and second light emitters 110 and 120 so that light is irradiated to the identified space by controlling the motor 150. The detailed description thereof will be described with reference to FIG. 4.

Figure 4:
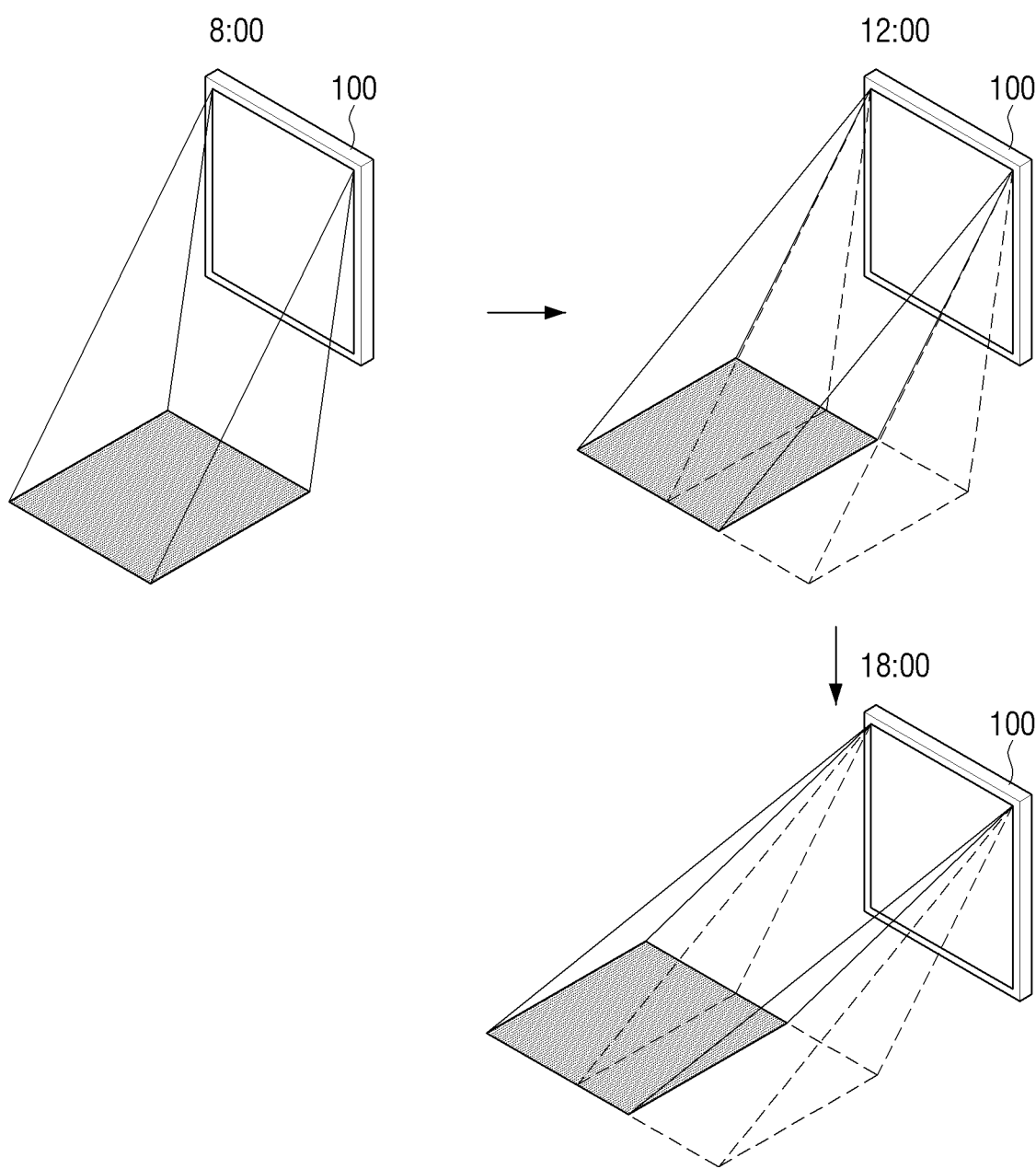
FIG. 4 is a diagram illustrating a change in a light emission direction over time according to an embodiment of the disclosure.

FIG. 4 is a diagram illustrating a change in a light emission direction over time according to an embodiment of the disclosure.

The processor 130 according to one embodiment may identify current time information. For example, if the current time is prior to a predetermined time according to the current time information, the processor 130 may control the first and second light emitters 110 and 120 not to emit light. As another example, the processor 130 may, if the current time matches a predetermined time, control the first and second light emitters 110 and 120 to emit light. The predetermined time may refer to an alarm time set by a user, a sunrise time, or the like.

As another embodiment, the processor 130, if the present time matches a preset time, may control so that the first light emitter 110 and the second light emitter 120 do not emit light. Here, the preset time may refer to a sunset time.

Referring to FIG. 4, the light emitting device 100 according to an embodiment may include the motor 150 connected to the first light emitter 110 and the second light emitter 120. The motor 150 according to an embodiment may be a motor capable of reciprocal rotational movement. The motor 150 may be implemented in various forms including a stepper motor, direct current (DC) motor, and a servo motor. The stepper motor is an electric motor which rotates at a certain angle by the voltage of a pulse shape.

The processor 130 may control the motor 150 to adjust the light emission direction of the first and second light emitters 110 and 120 connected to the motor 150 within a predetermined angle. For example, the processor 130 may control the motor so that the light emission direction of the first and second light emitters 110 and 120 is adjusted toward the left side with respect to the front surface of the light emitting device 100. As another example, the processor 130 may control the motor 150 so that the light emission direction of the first and second light emitters 110 and 120 is controlled to face the right side of the light emitting device 100.

For example, the processor 130 may identify a space corresponding to the sunrise time among the space in which the light emitting device 100 is installed if the current time is identified as the sunrise time based on the current time information. Here, the space corresponding to the sunrise time may refer to a left space on the basis of the front surface of the light emitting device 100. However, the embodiment is not limited thereto, but may refer to a space set by a user or a right space based on the front surface of the light emitting device 100.

The processor 130 may then control the motor 150 to move the light emission direction of the first and second light emitters 110 and 120 over time. Referring to FIG. 4, the processor 130 may control the motor 150 so that the light emission direction of the first and second light emitters 110 and 120 is directed toward the left side of the light emitting device 100 when the current time is the sunrise time (e.g., 6 am). The processor 130 may control the motor 150 so that the light emission direction of the first and second light emitters 110 and 120 is directed toward a central space with respect to the front surface of the light emitting device 100 over time. The processor 130 may control the motor 150 so that the light emission direction of the first and second light emitters 110 and 120 is directed to the right space with respect to the front surface of the light emitting device 100 if the current time is a sunset time (e.g., 6 pm). The processor 130 may control the first and second light emitters 110 and 120 not to emit light after the sunset time.

The embodiment in which the first and second light emitters 110 and 120 are turned on at the sunrise time and the first and second light emitters 110 and 120 are turned off at the sunset time is merely exemplary and is not limited thereto. The processor 130 may control the light emission direction of the first and second light emitters 110 and 120 to move from a right space to a left space with respect to the front surface of the light emitting device 100 over time. The direction of light emission may be referred to as the direction of light irradiation, the direction of light incidence, or the like, but will be collectively referred to as a light emission direction for convenience.

The light emitting device 100 according to an embodiment may not emit light only to a specific region regardless of the passage of time, but may move the direction of light emission over time. The light emitting device 100 may provide light similar to natural light even in a space where natural light does not enter, such as an underground space or a closed space, and may provide a similar effect as the direction of incidence of light moves over time.

Returning to FIG. 1, the light emitting device 100 according to one embodiment may include a sensor 140. The processor 130 may adjust the threshold illuminance value based on the illuminance value of the light sensed through the sensor 140, and may control the light emission intensity of the plurality of light emitting elements included in each of the first and second light emitters 110 and 120 based on the adjusted threshold illuminance value. The detailed description thereof will be described with reference to FIG. 5.

Figure 5:
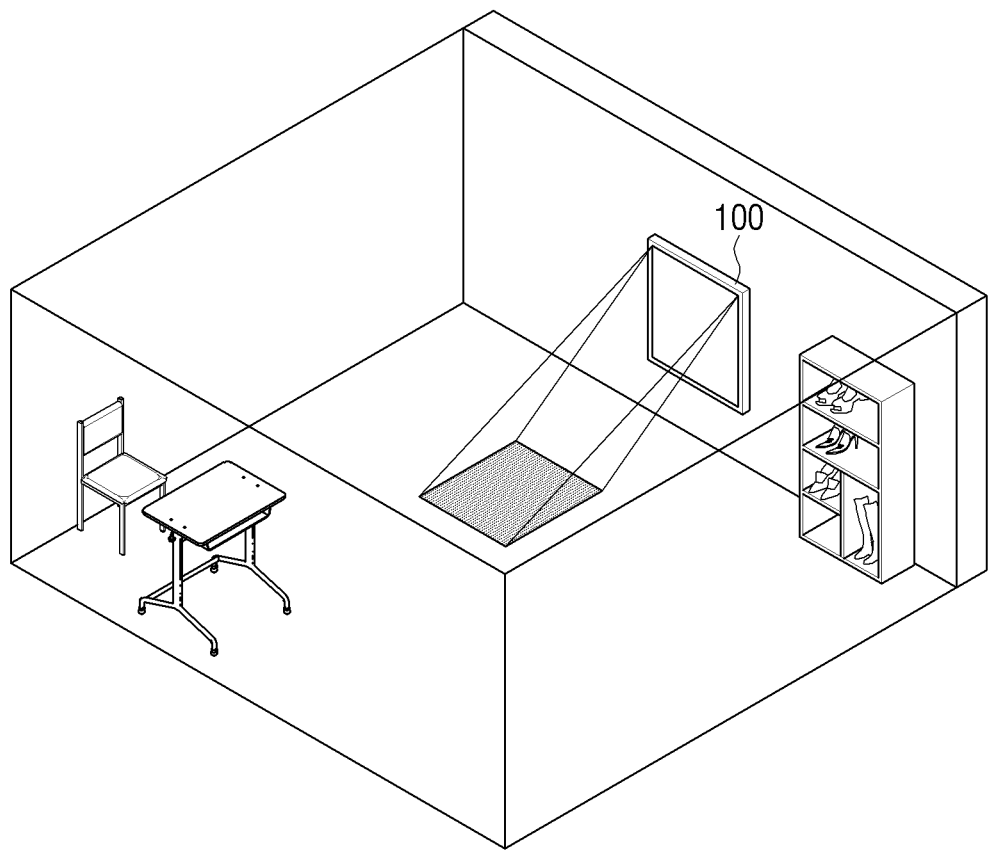
FIG. 5 is a diagram illustrating a threshold illuminance value according to an embodiment of the disclosure.

FIG. 5 is a diagram illustrating a threshold illuminance value according to an embodiment of the disclosure.

Referring to FIG. 5, the processor 130 may adjust the threshold illuminance value based on the illuminance value of the light sensed through the sensor 140. For example, the processor 130 may sense the illuminance value of light in a peripheral space where the light emitting device 100 is installed through the sensor 140. When the illuminance value of the light incident from the outside is sensed in the peripheral space in which the light emitting device 100 is installed, the processor 130 may lower the threshold illuminance value to less than 3000 lx based on the sensed illuminance value.

For example, if the light greater than or equal to a threshold illuminance value emitted from the light emitting device 100 is provided to the user in addition to the light incident from the outside, the user may feel discomfort or may be exposed to ultraviolet rays above the daily UV recommendation value. The processor 130 according to an embodiment may adjust a threshold illuminance value by sensing the intensity of light incident from the outside.

The light emitted from the light emitting device 100 according to an embodiment may belong to a range of 1500 to 10000 lx. The processor 130 according to an embodiment may control whether the light emitting device 100 emits light based on the intensity of light.

For example, the processor 130 may control the first and second light emitters 110 and 120 to emit light with the intensity of 10000 lx. The processor 130 may limit the light emitting time of the light emitting elements included in the first and second light emitters 110 and 120 within about 30 minutes.

As another example, the processor 130 may control the first and second light emitters 110 and 120 to emit light to with intensity of 3000 lx. The processor 130 may limit the light emitting time of the light emitting elements included in the first and second light emitters 110 and 120 to within about three hours. Here, the specific time is arbitrarily assumed for convenience and is not limited thereto. The processor 130 may control the light emitting time of the light emitting elements in inverse proportion to the intensity of the light. For example, the processor 130 may adjust the light emitting time of the light emitting elements to be relatively short as the intensity of the light increases, and may adjust the light emitting time of the light emitting elements to be relatively long as the intensity of the light decreases.

As described above, if light greater than or equal to a threshold illuminance value emitted from the light emitting device 100 is provided to the user for a long time, the user may feel discomfort or may be exposed to ultraviolet rays above the daily recommended reference value, and a problem such as a skin disease may occur. The processor 130 according to an embodiment may control at least one of whether light emitting elements emit light or a light emitting time based on the intensity of light emitted from the first and second light emitters 110 and 120. Returning to FIG. 1, the processor 130 according to an embodiment may identify color temperature information corresponding to at least one of a current time or a current weather and may control the intensity of at least one of a plurality of light emitting elements included in the first light emitter 110 to emit light corresponding to the identified color temperature. The detailed description thereof will be described with reference to FIG. 6.

Figure 6:
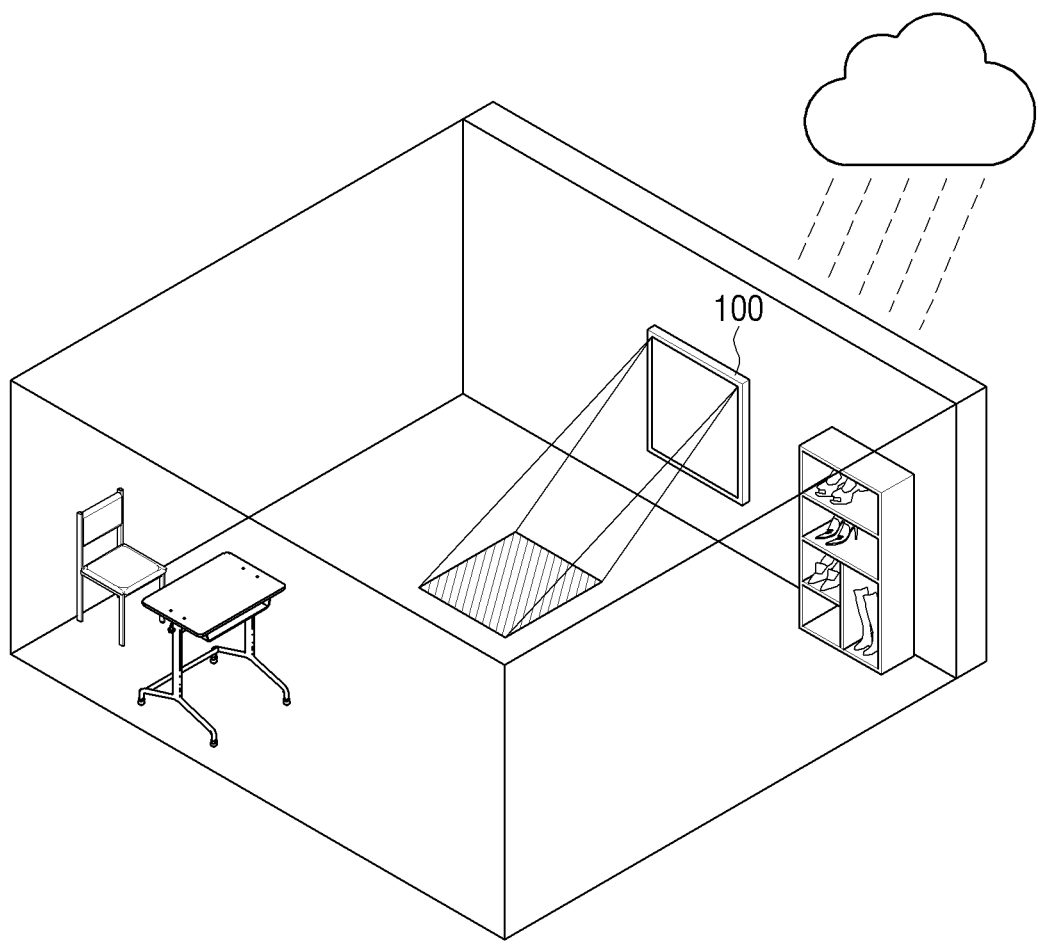
FIG. 6 is a diagram illustrating color temperature information according to an embodiment of the disclosure.

FIG. 6 is a diagram illustrating color temperature information according to an embodiment of the disclosure.

Referring to FIG. 6, the processor 130 according to one embodiment may identify color temperature information corresponding to at least one of a current time or a current weather. For example, the color temperature of natural light during sunrise may be 2000K, the color temperature of the natural light during sunset may be 2500K, the color temperature of the natural light at noon during a sunny day may be 5500K, and the color temperature of the natural light during a cloudy day may be 6500K to 6800K.

The processor 130 according to an embodiment may obtain color temperature-related information corresponding to at least one of current time, current weather, or current season based on the color temperature-related information corresponding to time, weather, or season.

The processor 130 may modulate a magnitude of a voltage applied to each of the plurality of light emitting devices included in the first light emitter 110. The processor 130 may control the emission intensity of each of the plurality of light emitting elements such that the color temperature of the light emitted from the first light emitter 110 may correspond to the color temperature identified according to at least one of the current time or the current weather.

For example, referring to FIG. 6, if the current weather is identified as a rainy and cloudy weather, the processor 130 may identify the color temperature 6500K corresponding to the cloudy weather. The processor 130 may control the emission intensity of each of the plurality of light emitting devices included in the first light emitter 110 such that the color temperature of the light emitted from the first light emitter 110 approaches 6500K. Since the user located in an indoor space is provided with light having a color temperature corresponding to the current weather, there is an effect of making the user recognize the external weather. The light emitting device 100 according to an embodiment may provide the user with light having a color temperature close to natural light for each time, weather, and season. The color temperature of the light emitted from the first light emitter 110 may be changed from 2000K to 6500K, but it is merely exemplary and is not limited thereto.

Returning to FIG. 1, the light emitting device 100 according to an embodiment may be implemented as a wall-hanging type installable on a wall and may include a structure in a window shape.

The processor 130 may control the first and second light emitters 110 and 120 whether to emit light or not based on a state of the structure in the window shape. This will be further described with reference to FIG. 7.

Figure 7:
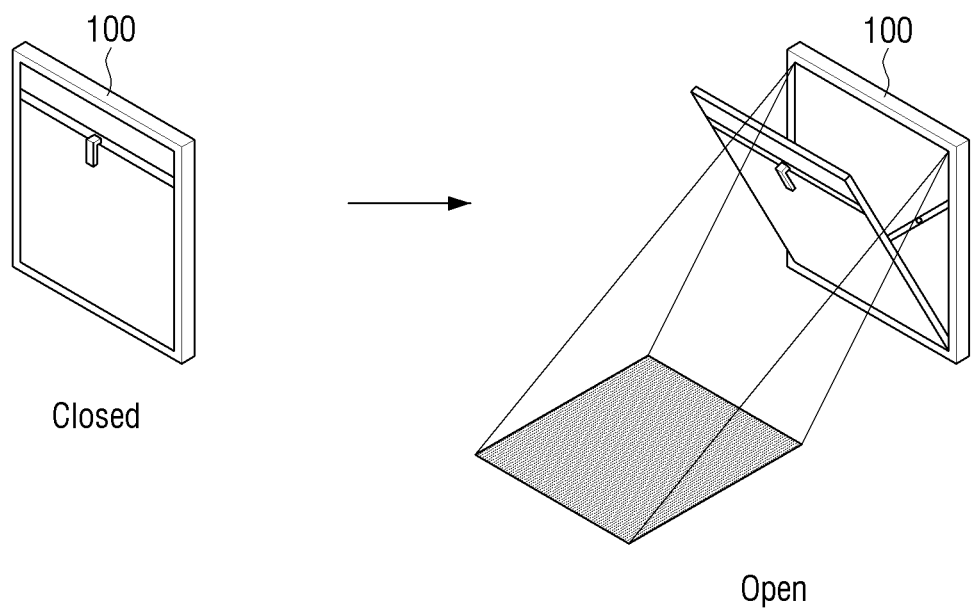
FIG. 7 is a diagram illustrating a shape of a light emitting device according to an embodiment of the disclosure.

FIG. 7 is a diagram illustrating a shape of a light emitting device according to an embodiment of the disclosure.

Referring to FIG. 7, the light emitting device 100 according to an embodiment may include a window-shaped structure. Here, the window-shaped structure may be changed to a first state or a second state. For example, the window-shaped structure may be changed to a first state, meaning an open state, and the window-shaped structure may be changed to a second state, meaning a closed state.

Based on an identification that the window-shaped structure is in the first state, the processor 130 according to an embodiment may control each of the first and second light emitters 110 and 120 to emit light. The processor 130, based on the window-shaped structure being the first state, may control the plurality of light emitting elements included in each of the first and second light emitters 110 and 120 to emit light by generating a turn-on signal for the light emitting device 100.

As another example, based on the window-shaped structure being a second state, the processor 130 may control the plurality of light emitting elements included in each of the first and second light emitters 110 and 120 not to emit light by generating a turn-off signal for the light emitting device 100.

The window-shaped structure shown in FIG. 7 is only one embodiment and is not limited thereto. For example, the window-shaped structure may be implemented with various shaped windows that can be opened and closed according to a user's manipulation or a signal received from a remote control device.

Returning to FIG. 1, the processor 130 according to an embodiment may further include a communication interface 160.

The communication interface 160 receives various signals. For example, the communication interface 160 may receive a signal by streaming or downloading from an external (for example, a source device), an external storage medium (for example, a universal serial bus (USB) device), an external server (for example, a web server, etc.) through communication methods such as, for example, and without limitation, an access point (AP)-based Wi-Fi (wireless LAN network), Bluetooth, Zigbee, wired/wireless local area network (LAN), wide area network (WAN), Ethernet, IEEE 1394, high definition multimedia interface (HDMI), universal serial bus (USB), mobile high-definition link (MHL), advanced encryption standard (AES)/European broadcasting union (EBU), optical, coaxial, or the like.

The communication interface 160 may communicate with a remote control device using various communication methods using radio frequency (RF) or infrared (IR), or the like, and may receive a control signal. This will be further described with reference to FIG. 8.

Figure 8:
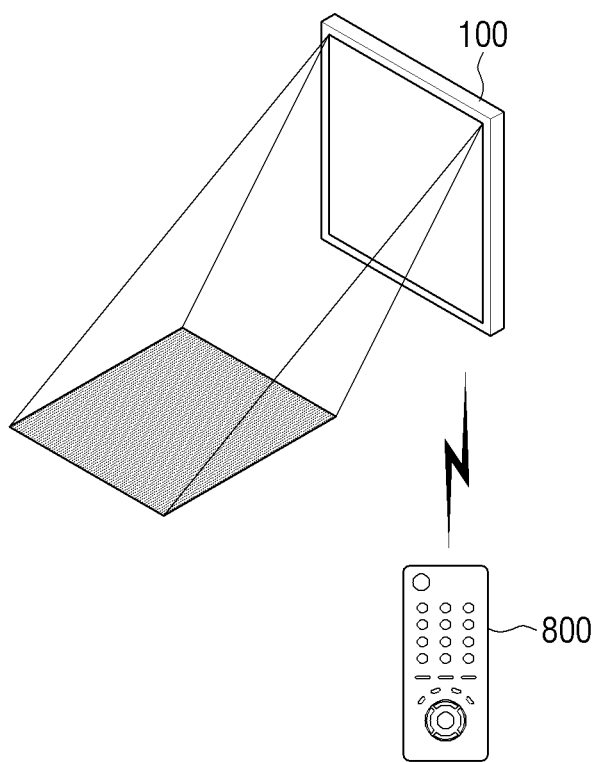
FIG. 8 is a diagram illustrating a light emitting device in communication with a remote control device according to an embodiment of the disclosure.

FIG. 8 is a diagram illustrating a light emitting device in communication with a remote control device 800 according to an embodiment of the disclosure.

Referring to FIG. 8, the light emitting device 100 according to one embodiment may receive a control signal from a remote control device 800 via the communication interface 160. The processor 130 may control at least one of light emission of each of the first light emitter 110 and the second light emitter 120, a threshold illuminance value, a color temperature of light emitted from the first light emitter 110, and a light emission direction of each of the first and second light emitters 110 and 120 based on the control signal.

For example, the processor 130 may set a preset time based on a control signal received from the remote control device 800. The preset time may refer to an alarm time. The processor 130 may set the light emission start time or light emission end time of the first and second light emitters 110 and 120 based on the preset time.

As another example, the processor 130 may control at least one of the light emission directions of each of the first and second light emitters 110 and 120 based on a control signal received from the remote control device 800. For example, the processor 130 may control the motor 150 to emit light only to a particular region regardless of the passage of time based on the control signal. As another example, the processor 130 may control the rotation of the motor 150 so that light is emitted from the right region to the left region with respect to the front surface of the light emitting device 100 over time.

The embodiment is not limited thereto and each of the plurality of functions that can be performed by the light emitting device 100 may be controlled by the remote control device 800.

The display may be implemented as a display of various types such as, for example, and without limitation, a liquid crystal display (LCD), organic light emitting diodes (OLED) display, light emitting diodes (LED), micro LED, quantum dot light emitting diodes (QLED), liquid crystal on silicon (LCoS), digital light processing (DLP), quantum dot (QD) display, or the like. The light emitting device 100 may output a content and an image signal through a display according to an embodiment.

Figure 9:
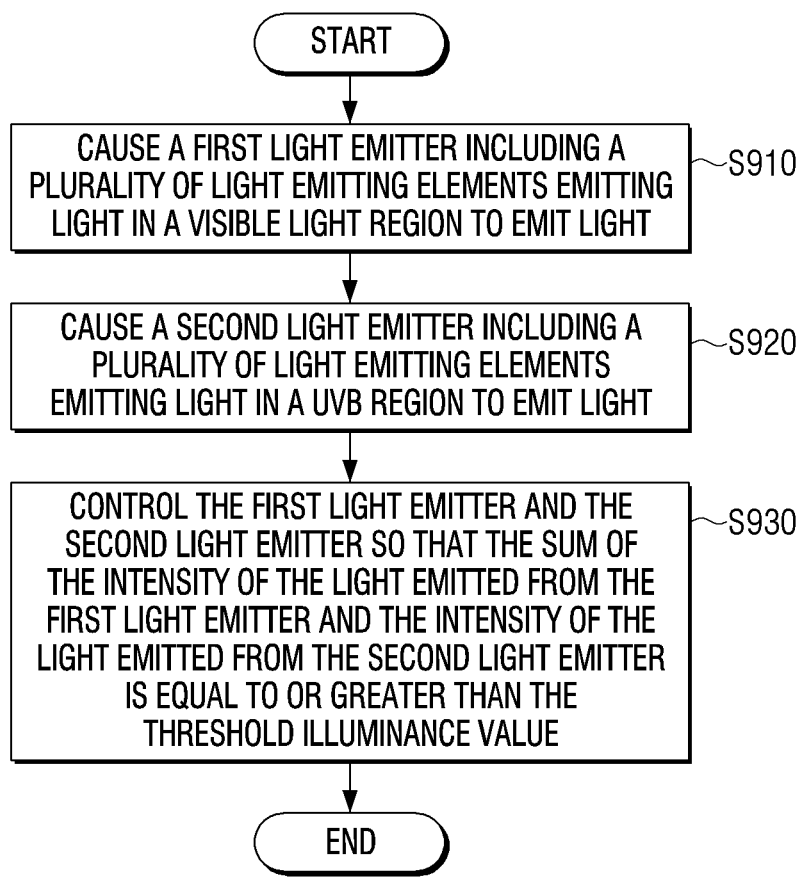
FIG. 9 is a flow chart illustrating a control method of a light emitting device according to an embodiment of the disclosure.

FIG. 9 is a flow chart illustrating a control method of a light emitting device according to an embodiment of the disclosure.

Referring to FIG. 9, a control method of a light emitting device emits a first light emitter including a plurality of light emitting elements emitting light in a visible light region in operation S910. Then, a second light emitter including a plurality of light emitting devices emitting light of the UVB region is emitted in operation S920. The first light emitter and the second light emitter are controlled so that the sum of the intensity of the light emitted from the first light emitter and the intensity of the light emitted from the second light emitter is equal to or greater than the threshold illuminance value in operation S930.

The light emitting element having a threshold value or higher, among the plurality of light emitting elements included in the first light emitter may be implemented as a white light emitting element and remaining light emitting elements among the plurality of light emitting elements may be implemented as at least one of the red light emitting element, green light emitting element, or blue light emitting element.

According to an embodiment, the light emitting device may further include a first light collector disposed on the front surface of the first light emitter to collect and irradiate light emitted from the first light emitter and a second light collector disposed on the front surface of the second light emitter to collect and irradiate light emitted from the second light emitter, wherein the light irradiated from each of the first and second light collector may have straightness.

The light emitting device may further include a motor connected to the first and second light emitters, and the control method according to an embodiment may further include the step of identifying one space among the spaces in which the light emitting device is installed based on the current time information, and adjusting the light emission direction of the first and second light emitters so that the light is irradiated to the identified space by controlling the motor.

The light emitting device is implemented as a device installable on a wall, and the first light emitter may be disposed at one side of the light emitting device and the second light emitter may be disposed to be adjacent to the first light emitter on one side of the light emitting device.

The light emitting device may further include a sensor.

The controlling operation S930 according to an embodiment may include the steps of adjusting a threshold illuminance value based on an illuminance value of light sensed through a sensor and controlling a light emitting intensity of a plurality of light emitting elements included in each of the first light emitter and the second light emitter based on the adjusted threshold illuminance value.

The plurality of light emitting devices included in the first light emitter includes a white light emitter, a red light emitter, a green light emitter, and a blue light emitter, and the control method according to an embodiment may further include identifying color temperature information corresponding to at least one of a current time or a current weather, and the controlling in operation S930 may include controlling the intensity of at least one light emitting element among the plurality of light emitting elements to emit light corresponding to the identified color temperature.

The light emitting device is implemented in a form of a wall-hanging type installable on a wall, and may include a window-shaped structure, and the controlling in operation S930 may include controlling the first and second light emitters to emit light when the first and second light emitters are identified as being in the first state of the window-shaped structure, and controlling the first and second light emitters not to emit light when the first and second light emitters are identified as being in the second state of the window-shaped structure.

In operation S930, when the control signal is received, the controlling step may include controlling at least one of the light emission of each of the first and second light emitters, the threshold illuminance value, the color temperature of the light emitted from the first light emitter, or the light emission direction of each of the first and second light emitters based on the control signal.

Figure 10:
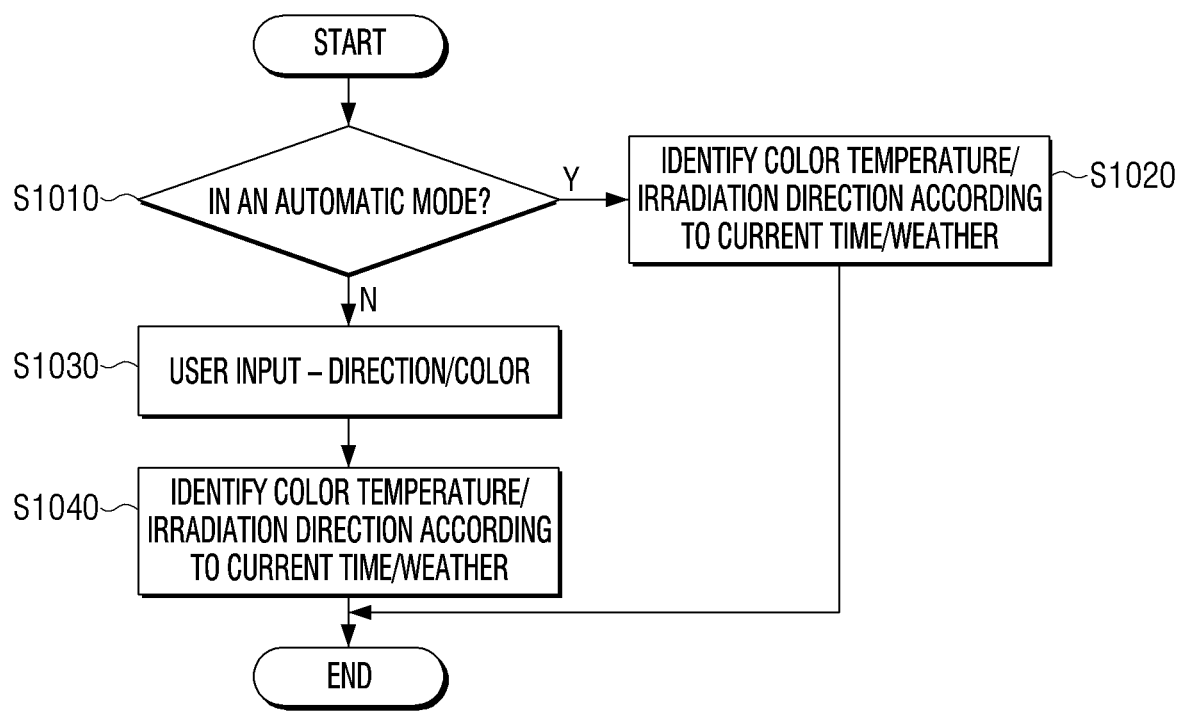
FIG. 10 is a flowchart illustrating an operation of a light emitting device in an automatic mode according to an embodiment of the disclosure.

FIG. 10 is a flowchart illustrating an operation of a light emitting device in an automatic mode according to an embodiment of the disclosure.

Referring to FIG. 10, the light emitting device 100 according to an embodiment may identify whether the light emitting device 100 is in an automatic mode in operation S1010.

If the light emitting device 100 is in an automatic mode in operation S1010-Y, the illumination direction of light or color temperature corresponding to the current time or current weather is identified in operation S1020.

If the light emitting device 100 is not in an automatic mode in operation S1010-N, the user's input is received in operation S1030. Subsequently, the control method according to one embodiment may include identifying the color temperature or the direction of illuminance of the light in operation S1040 based on the user input in operation S1030.

The automatic mode may be turned on/off according to the user's setting. For example, if the light emitting device 100 is changed from the automatic mode to the normal mode according to the user's setting, the light emitting state of the first and second light emitters 110 and 120, the color temperature of the emitted light, and the light emission direction may be changed according to the control of the user.

In another example, the light emitting device 100 may include a partial automatic mode in addition to automatic mode and normal mode. For example, the partial automatic mode may automatically identify only the color temperature corresponding to the current time or current weather, and the light emission direction, the threshold illuminance value, or the like, may be changed according to the user's settings. As another example, only the light emission direction may be automatically adjusted over time, and the remaining settings may be changed according to the user's control.

The various embodiments may be applicable to not only light emitting devices but also all types of electronic devices including a light emitting element.

The various example embodiments described above may be implemented in a recordable medium which is readable by computer or a device similar to computer using software, hardware, or the combination of software and hardware. In some cases, embodiments described herein may be implemented by the processor itself. According to a software implementation, embodiments such as the procedures and functions described herein may be implemented with separate software modules. Each of the above-described software modules may perform one or more of the functions and operations described herein.

The computer instructions for performing the processing operations of the light emitting device 100 according to the various embodiments described above may be stored in a non-transitory computer-readable medium. The computer instructions stored in this non-transitory computer-readable medium cause the above-described specific device to perform the processing operations of the light emitting device 100 according to the above-described various embodiments when executed by the processor of the specific device.

The non-transitory computer readable medium may refer, for example, to a medium that stores data, such as a register, a cache, a memory or etc., and is readable by a device. For example, the aforementioned various applications, instructions, or programs may be stored in the non-transitory computer readable medium, for example, a compact disc (CD), a digital versatile disc (DVD), a hard disc, a Blu-ray disc, a universal serial bus (USB), a memory card, a read only memory (ROM), and the like, and may be provided.

While the disclosure has been shown and described with reference to various embodiments thereof, it will be understood by those of skilled in the art that various changes in form and details may be made therein without departing from the spirit and scope of the disclosure as defined by the appended claims and their equivalents.

What is claimed is:

1. A light emitting device comprising:
    a first light emitter comprising a plurality of light emitting elements configured to emit light in a visible light region;
    a second light emitter comprising a plurality of light emitting elements configured to emit light in an ultraviolet B (UVB) region; and
    at least one processor configured to control the first light emitter and the second light emitter so that a sum of an intensity of light emitted from the first light emitter and an intensity of light emitted from the second light emitter is greater than or equal to a threshold illuminance value,
    wherein the light emitting device is implemented as a wall-hanging type installable on a wall and comprises a window-shaped structure, and
    wherein the at least one processor is further configured to:
        identify a state of the window-shaped structure,
        control each of the first light emitter and the second light emitter to emit light based on an identification that the state of the window-shaped structure is a first state, and
        control each of the first light emitter and the second light emitter not to emit light based on an identification that the state of the window-shaped structure is a second state.

2. The light emitting device of claim 1,
    wherein the plurality of light emitting elements of the first light emitter include a white light emitting element and at least one remaining light emitting element,
    wherein a ratio of an intensity of light emitted by the white light emitting element to an intensity of light emitted by the at least one remaining light emitting element is greater than or equal to a threshold ratio, and
    wherein the at least one remaining light emitting element is implemented as at least one of a red light emitting element, a green light emitting element, or a blue light emitting element.

3. The light emitting device of claim 1, further comprising:
    a first light collector disposed in a front surface of the first light emitter, the first light collector configured to collect and irradiate light emitted from the first light emitter; and
    a second light collector disposed in a front surface of the second light emitter, the second light collector configured to collect and irradiate light emitted from the second light emitter,
    wherein light irradiated from each of the first light collector and the second light collector has straightness.

4. The light emitting device of claim 3, further comprising:
    a motor connected to the first light emitter and the second light emitter,
    wherein the at least one processor is further configured to:
        identify a space among spaces in which the light emitting device is installed based on current time information, and
        control the motor to adjust a light emission direction of the first light emitter and the second light emitter so as to irradiate the identified space with light.

5. The light emitting device of claim 1,
    wherein the light emitting device is implemented as a device installable on a wall,
    wherein the first light emitter is disposed on one side of the light emitting device, and
    wherein the second light emitter is disposed to be adjacent to the first light emitter on the one side of the light emitting device.

6. The light emitting device of claim 1, further comprising:
    a sensor,
    wherein the at least one processor is further configured to:
        adjust the threshold illuminance value based on an illuminance value of light sensed through the sensor, and
        control the intensity of light emitted from the first light emitter and the intensity of light emitted from the second light emitter based on the adjusted threshold illuminance value.

7. The light emitting device of claim 1,
wherein the plurality of light emitting elements included in the first light emitter comprise a white light emitting element, a red light emitting element, a green light emitting element, and a blue light emitting element, and
wherein the at least one processor is further configured to:
identify color temperature information corresponding to at least one of a current time or a current weather, and
control an intensity of at least one light emitting element among the plurality of light emitting elements included in the first light emitter to emit light corresponding to the identified color temperature.

8. The light emitting device of claim 1, further comprising:
a communication interface configured to receive a control signal,
wherein the at least one processor is further configured to control at least one of whether to emit light by each of the first light emitter and the second light emitter, the threshold illuminance value, a color temperature of light emitted from the first light emitter, or a light emission direction of each of the first light emitter and the second light emitter based on the control signal.

9. A control method of a light emitting device, the method comprising:
causing a first light emitter comprising a plurality of light emitting elements configured to emit light in a visible light region to emit light;
causing a second light emitter comprising a plurality of light emitting elements configured to emit light in an ultraviolet B (UVB) region to emit light; and
controlling the first light emitter and the second light emitter so that a sum of intensity of light emitted from the first light emitter and intensity of light emitted from the second light emitter is greater than or equal to a threshold illuminance value,
wherein the light emitting device is implemented as a wall-hanging type installable on a wall and comprises a window-shaped structure, and
wherein the controlling comprises:
identifying a state of the window-shaped structure;
controlling each of the first light emitter and the second light emitter to emit light based on an identification that the state of the window-shaped structure is a first state; and
controlling each of the first light emitter and the second light emitter not to emit light based on an identification that the state of the window-shaped structure is a second state.

10. The method of claim 9,
wherein the plurality of light emitting elements of the first light emitter include a white light emitting element and at least one remaining light emitting element,
wherein a ratio of an intensity of light emitted by the white light emitting element to an intensity of light emitted by the at least one remaining light emitting element is greater than or equal to a threshold ratio, and
wherein the at least one remaining light emitting element is implemented as at least one of a red light emitting element, a green light emitting element, or a blue light emitting element.

11. The method of claim 9,
wherein the light emitting device further comprises:
a first light collector disposed in a front surface of the first light emitter, the first light collector configured to collect and irradiate light emitted from the first light emitter; and
a second light collector disposed in a front surface of the second light emitter, the second light collector configured to collect and irradiate light emitted from the second light emitter, and
wherein light irradiated from each of the first light collector and the second light collector has straightness.

12. The method of claim 11,
wherein the light emitting device further comprises a motor connected to the first and second light emitters, and
wherein the method further comprises:
identifying a space among spaces in which the light emitting device is installed based on current time information, and
controlling the motor to adjust a light emission direction of the first light emitter and the second light emitter so as to irradiate the identified space with light.

13. The method of claim 12, further comprising:
identifying a current weather condition; and
adjusting a color temperature of light emitted from the first light emitter based on the identified current weather condition.

14. The method of claim 13, wherein the identifying of the current weather condition comprises:
receiving, through a communication interface, current weather information, and
identifying the current weather condition based on the current weather information.

15. The method of claim 9,
wherein the light emitting device is implemented as a device installable on a wall,
wherein the first light emitter is disposed on one side of the light emitting device, and
wherein the second light emitter is disposed to be adjacent to the first light emitter on the one side of the light emitting device.

16. The method of claim 9,
wherein the light emitting device further comprises a sensor,
wherein the controlling comprises:
adjusting the threshold illuminance value based on an illuminance value of light sensed through the sensor; and
controlling the intensity of light emitted from the first light emitter and the intensity of light emitted from the second light emitter based on the adjusted threshold illuminance value.

17. The method of claim 9,
wherein the plurality of light emitting elements included in the first light emitter comprise a white light emitting element, a red light emitting element, a green light emitting element, and a blue light emitting element,
wherein the method further comprises identifying color temperature information corresponding to at least one of a current time or a current weather, and
wherein the controlling of the first light emitter and the second light emitter comprises controlling an intensity of at least one light emitting element among the plurality of light emitting elements included in the first light emitter to emit light corresponding to the identified color temperature.

18. The method of claim 9, wherein the controlling comprises:
   based on receiving a control signal, controlling at least one of whether to emit light of each of the first light emitter and the second light emitter, the threshold illuminance value, a color temperature of light emitted from the first light emitter, or a light emission direction of each of the first light emitter and the second light emitter based on the control signal.

* * * * *